United States Patent [19]

Mosher et al.

[11] Patent Number: 4,585,859

[45] Date of Patent: Apr. 29, 1986

[54] ANALOGUES OF MORPHOLINYL DAUNORUBICIN AND MORPHOLINYL DOXORUBICIN

[75] Inventors: Carol W. Mosher, Stanford; George L. Tong, Cupertino; Edward M. Acton, Menlo Park, all of Calif.

[73] Assignee: SRI International, Menlo Park, Calif.

[21] Appl. No.: 598,016

[22] Filed: Apr. 9, 1984

Related U.S. Application Data

[63] Continuation-in-part of Ser. No. 496,122, May 24, 1983, Pat. No. 4,464,529, which is a continuation-in-part of Ser. No. 400,120, Jul. 20, 1982, abandoned.

[51] Int. Cl.$^4$ ............................................. C07H 15/24
[52] U.S. Cl. ....................................................... 536/6.4
[58] Field of Search .......................................... 536/6.4

[56] References Cited

U.S. PATENT DOCUMENTS

| | | | |
|---|---|---|---|
| 4,202,967 | 5/1980 | Tong et al. | 536/6.4 |
| 4,301,277 | 11/1981 | Acton et al. | 536/6.4 |
| 4,314,054 | 2/1982 | Acton et al. | 536/6.4 |
| 4,464,529 | 8/1984 | Mosher et al. | 536/6.4 |

FOREIGN PATENT DOCUMENTS

| | | | |
|---|---|---|---|
| 0128670 | 12/1984 | European Pat. Off. | 536/6.4 |
| 2140006 | 11/1984 | United Kingdom | 536/6.4 |

*Primary Examiner*—Johnnie R. Brown
*Assistant Examiner*—Elli Peselev
*Attorney, Agent, or Firm*—Ciotti & Murashige

[57] ABSTRACT

A group of new daunorubicin and doxorubicin derivatives is disclosed. Included in this group are 3'-deamino-3'(3"-cyano-4"-morpholinyl) doxorubicin; 3'-deamino-3'-(3"-cyano-4"-morpholinyl)-13-dihydoxorubicin; (3'-deamino-3'-(3"-cyano-4"-morpholinyl) daunorubicin; 3'-deamino-3'-(3"-cyano-4"-morpholinyl)-3-dihydrodaunorubicin; and 3'-deamino-3'-(4"-morpholinyl-5-iminodoxorubicin and derivatives thereof which have excellent activity as antitumor agents.

8 Claims, No Drawings

ANALOGUES OF MORPHOLINYL DAUNORUBICIN AND MORPHOLINYL DOXORUBICIN

ORIGIN OF THE INVENTION

The invention described herein was made in the course of work under National Cancer Institute Grant No. CA25711 and CA32250 of the Department of Health and Human Services.

REFERENCE TO RELATED APPLICATION

This is a continuation in part of copending U.S. application Ser. No. 496,122, filed May 24, 1983 now U.S. Pat. No. 4,464,529, which is, in turn, a continuation in part of U.S. application Ser. No. 400,120, filed July 20, 1982, and now abandoned.

DESCRIPTION

1. Technical Field

This invention is in the field of anthracycline chemistry. More particularly it concerns analogues of the anthracyclines doxorubicin and daunorubicin that are useful as antitumor agents.

2. Background Art

Doxorubicin (adriamycin) is perhaps the most useful new anticancer drug in use at this time. It (along with daunorubicin) is a principal agent in the treatment of an unusually wide number of solid tumors and leukemias. Regrettably, many patients with these tumors fail to respond and essentially no patients with some serious tumor types (colon cancer, melanoma) respond. In addition, in some patients chronic treatment produces irreversible heart damage that can be fatal if continued. Thus, there is great need for analogues which give a better rate of response, a wider spectrum of response, or reduced cardiotoxicity. More effective and less toxic agents are widely sought and are the fundamental object of this invention. The most active new analogues so far, judging from screening results in a widely used test against mouse leukemia P388 in a 3-dose treatment schedule (q4d 5,9,13), are two lipophilic derivatives (AD32 and N,N-dibenzyldaunorubicin) that required significantly higher doses, and that fail to interact with DNA in vitro although DNA is believed to be a primary biological target for the anthracycline series. Most N-alkyl derivatives have been active in the antitumor screen against mouse leukemia P388, but are not significantly different from doxorubicin or daunorubicin. A few such derivatives have been inactive.

Much of the history and prior art of doxorubicin and its anthracycline analogues is found in the article "Adriamycin" by David W. Henry, *ACS Symposium Series, No. 30, Cancer Chemotherapy*, American Chemical Society, pp. 15–57 (1976) and in the book *Doxorubicin* by Frederico Arcamone, Academic Press, 1981. AD32 is disclosed in U.S. Pat. No. 4,035,566, dated July 12, 1977.

5-Iminodaunorubicin is shown in U.S. Pat. No. 4,109,076 which issued on Aug. 22, 1978, to David W. Henry and George L. Tong and which is assigned to the assignee of the present invention. The doxorubicin equivalent is shown in "Synthesis and Preliminary Antitumor Evaluation of 5-Iminodoxorubicin", *J. Medicinal Chem.*, 24, 669 (1981) by Edward M. Acton and George L. Tong. 5-Iminodaunorubicin retained activity with reduced side effects while 5-iminodoxorubicin showed enhanced activity but required higher dosages.

3'-Deamino-3'-(4-morpholinyl)daunorubicin, disclosed in U.S. Pat. No. 4,301,277 issued on Nov. 17, 1981 to Edward M. Acton and Carol W. Mosher and assigned to the assignee of the present invention, was active at one-fortieth the dose of doxorubicin but gave a substantially identical T/C value (166% vs 160% against P388). This compound and its preparation and properties are also disclosed in "Enhanced Antitumor Properties of 3'-(4-Morpholinyl) and 3'-(4-Methoxy-1-piperidinyl) Derivatives of 3'-Deaminodaunorubicin", *J. Medicinal Chem.*, 25, pp. 18–24 (1982) by Carol W. Mosher, Helen Y. Wu, Allan N. Fujiwara and Edward M. Acton.

A general reductive alkylation process for preparing new semi-synthetic anthracycline derivatives is described in "Adriamycin Analogs. 3. Synthesis of N-Alkylated Anthracyclines With Enhanced Efficacy and Reduced Cardiotoxicity", *J. Medicinal Chem.*, 22, pp. 912–918 (1979) by G. L. Tong, H. Y. Wu, T. H. Smith and D. W. Henry.

The subject matter of this prior art is specifically incorporated herein by reference.

STATEMENT OF THE INVENTION

A group of new daunorubicin and doxorubicin derivatives has now been found. These compounds are represented by the General Formula I

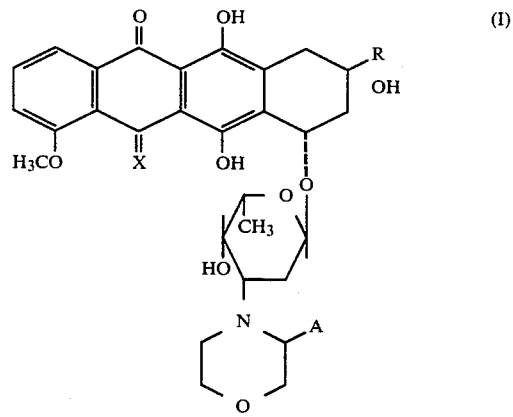

wherein R is CO—CH$_3$ or CHOH—CH$_3$ in the case of daunorubicin derivatives or CO—CH$_2$OH or CHOH—CH$_2$OH in the case of doxorubicin derivatives; X is O or NH; and A is either a cyano group (CN) or a hydrogen, subject to the limitation that when X is O, A must be a cyano group. When A is hydrogen, these compounds can exist as acid addition salts, as well. These salts are an additional aspect of this invention.

In another, broader aspect the invention provides derivatives of these compounds which derivatives have been formed by one or more modifications shown in the art to be effective with analogous daunorubicin and doxorubicin materials. Such modifications involve further changes in the R group, removal of the 4 position methoxy, changes in the 4' carbon substituents, changes in A and substitution in the morpholinyl ring. The compounds encompassed by these various derivitizations are generally classified as morpholinyl or analogues of morpholinyl derivatives of daunorubicin and doxorubicin type materials and are represented by the General Formula II

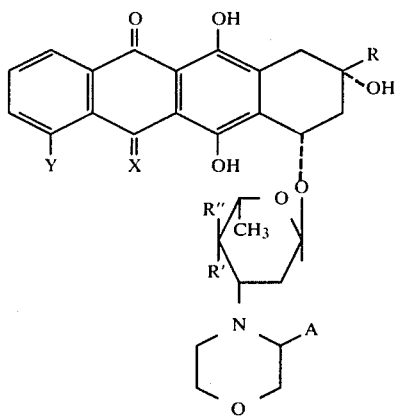

(II)

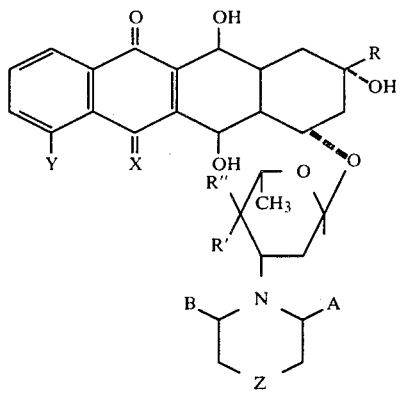

III wherein R is —CO—CH₃ or —CHOH—CH₃ in the case of simple daunorubicin derivatives, —CO—CH₂OH or —CHOH—CH₂OH in the case of simple doxorubicin derivatives; hydroxy; a 1 to 3 carbon alkyl, such as —CH₂CH₃; a 1 to 3 carbon terminal hydroxyalkyl such as —CH₂—OH or —CH₂—CH₂—OH; 2 to 7 carbon organic acidbased esters and diesters of —CO—CH₂OH, —CHOH—CH₂OH, and —CHOH—CH₃ including for example acetate (—OAc), propionate (—OPr), benzoate (—OBz) and glycolate (—O—Gl) esters such as —CO—CH₂—OAc, —CO—CH₂—OBz, —CO—CH₂—OPr, —CO—CH₂—OGl, —CH(OAc)—CH₂—OAc, —CH(OBz)—CH₂—OBz, —CH(OAc)CH₃, and —CH(OBz)CH₃ or the like; a 1 to 6 carbon alkyl or aryl ether replacement of one or more hydroxyls of —CO—CH₂OH, —CHOH—CH₃, and —CHOH—CH₂OH, such as —CH(OCH₃)—CH₃, —CO—CH₂O—CH₃, —CO—CH₂O—C₂H₅, —CO—CH₂O—C₆H₅ or the like; and 13-ketimine derivatives of —CO—CH₃ or —CO—CH₂OH such as —C(NOH)—CH₃, —C(NNHBz)CH₃, —C(NOCH₃)—CH₃, —C(NOH)—CH₂OH, —C(NOCH₃)—CH₂OH, and —C(NNHBz)—CH₂OH or the like; Y is usually methoxy (—OCH₃) but can also be hydrogen, X is =O or =NH; R' and R" together are a hydrogen and a hydroxy (that is, either R' or R" is hydroxy with the other hydrogen), both are hydrogens or R' is O-methoxy and R" is hydrogen; and A is selected from cyano (—C≡N) and hydrogen as set forth above. When A is hydrogen, these compounds can exist as acid addition salts, as well. Z is selected from oxygen, sulfur,

wherein R'''is a 1 to 3 carbon alkyl, and —CH₂— subject to the proviso that when Z is —CH₂— or

A is —C≡N.

Another, still broader aspect of the invention relates to analogs of morpholinyl derivatives of daunorubicin and doxorubicin which have the formula wherein R is —CO—CH₃ or —CHOH—CH₃ in the case of simple daunorubicin derivatives, —CO—CH₂OH or —CHOH—CH₂OH in the case of simple doxorubicin derivatives; hydroxy; a 1 to 3 oarbon alkyl, such as —CH₂CH₃; a 1 to 3 carbon terminal hydroxyalkyl such as —CHOH or —CH₂—CH₂—OH; 2 to 7 carbon organic acid-based esters and diesters of —CO—CH₂OH, —CHOH—CH₂OH, and —CHOH—CH₃ including, for example, acetate (—OAc), propionate (—OPr), benzoate (—OBz) and glycolate (—O—Gl) esters such as —CO—CH₂—OAc, —CO—CH₂—OBz, —CO—CH₂—OPr, —CO—CH₂—OGl, —CH(OAc)—CH₂—OAc, —CH(OBz)—CH₂—OBz, —CH(OAc)CH₃, and —CH(OBz)CH₃ or the like; a 1 to 6 carbon alkyl or aryl ether replacement of one or more hydroxyls of —CO—CH₂OH, —CHOH—CH₃, and —CHOH—CH₂OH, such as —CH(OCH₃)—CH₃, —CO—CH₂O—CH₃, —CO—CH₂O—C₂H₅, —CO—CH₂O—C₆H₅ or the like; and 13-ketimine derivatives of —CO—CH₃ or —CO—CH₂OH such as —C(NOH)—CH₃, —C(NNHBz)CH₃, —C(NOCH₃)—CH₃, —C(NOH)—CH₂OH, —C(NOCH₃)—CH₂OH, and —C(NNHBz)—CH₂OH or the like;

Y is usually methoxy (—OCH₃) but can also be hydrogen, X is =O or =NH;

B is H or CN, or B and the hydrogen bonded to the same carbon taken together are =O;

R' and R" together are a hydrogen and a hydroxy (that is, either R' or R" is hydroxy with the other hydrogen), both are hydrogens, or R' is O-methoxy and R" is hydrogen; or B and R' taken together are the oxygen bridge —O—;

A is selected from cyano (—C≡N) and hydrogen as set forth above; Z is selected from oxygen, sulfur,

wherein R''' is a 1 to 3 carbon alkyl, and —CH₂—, subject to the proviso that when Z is —CH₂— or

A as —C≡N;

and any of their pharmaceutically acceptable acid addition salts.

These compounds are related to the established anticancer drugs daunorubicin and doxorubicin (adriamycin), are prepared from them by chemical synthesis and derivatization techniques, and are active agents against cancer. They appear to combine two advantageous and sought-after properties—high antitumor efficacy and low dose requirements. Thus, they offer the promise of high effectiveness with reduced dose-related side effects such as cardiotoxicity as compared with materials disclosed heretofore.

In other aspects, this invention provides pharmaceutical preparations containing these new derivatives as well as a method for treating mammalian cancer by administering such preparations to a mammal in need of such treatment.

DETAILED DESCRIPTION OF THE INVENTION

The present invention provides morpholinyl derivatives of iminodaunorubicin and iminodoxorubicin and the pharmaceutically acceptable salts therof as well as cyanomorpholinyl derivatives of daunorubicin, doxorubicin, iminodaunorubicin and iminodoxorubicin. These compounds are listed in Table I.

TABLE I
Compounds of the Invention

| X | A | R | Compound Name |
|---|---|---|---|
| NH | H | CO—CH$_3$ | 3'-deamino-3'-(4''-morpholinyl)-5-iminodaunorubicin and pharmaceutically acceptable salts thereof |
| NH | H | CHOH—CH$_3$ | 3'-deamino-3'-(4''-morpholinyl)-13-dihydro-5-iminodaunorubicin and pharmaceutically acceptable salts thereof |
| NH | H | CO—CH$_2$OH | 3'-deamino-3'-(4''-morpholinyl)-5-iminodoxorubicin and pharmaceutically acceptable salts thereof |
| NH | H | CHOH—CH$_2$OH | 3'-deamino-3'-(4''-morpholinyl)-13-dihydro-5-iminodoxorubicin and pharmaceutically acceptable salts thereof |
| O | CN | CO—CH$_3$ | 3'-deamino-3'-(3''-cyano-4''-morpholinyl)daunorubicin |
| O | CN | CHOH—CH$_3$ | 3'-deamino-3'-(3''-cyano-4''-morpholinyl)-13-dihydrodaunorubicin |
| O | CN | CO—CH$_2$OH | 3'-deamino-3'-(3''-cyano-4''-morpholinyl)doxorubicin |
| O | CN | CHOH—CH$_2$OH | 3'-deamino-3'-(3''-cyano-4''-morpholinyl)-13-dihydrodoxorubicin |
| NH | CN | CO—CH$_3$ | 3'-deamino-3'-(3''-cyano-4''-morpholinyl)-5-iminodaunorubicin |
| NH | CN | CHOH—CH$_3$ | 3'-deamino-3'-(3''-cyano-4''-morpholinyl)-13-dihydro-5-iminodaunorubicin |
| NH | CN | CO—CH$_2$OH | 3'-deamino-3'-(3''-cyano-4''-morpholinyl)-5-iminodoxorubicin |
| NH | CN | CHOH—CH$_2$OH | 3'-deamino-3'-(3''-cyano-4''-morpholinyl)-13-dihydro-5-iminodoxorubicin |

Also included as compounds of the invention are:

| X | A | R | R'B | Compound Name |
|---|---|---|---|---|
| 0 | CN | COCH$_2$OH | —O— | 3'-deamino-5'',4'-anhydro-3'-(5''-hydroxy-3''-cyano-4''-morpholinyl) doxorubicin |
| 0 | CN | COCH$_2$OH | —OH,—CN | 3'-deamino-3'-(3'', 5''-dicyano-4''-morpholinyl) doxorubicin |
| 0 | CN | COCH$_2$OH | —OH,—OH | 3'-deamino-3'-(5''hydroxy-3''-cyano-4''-morpholinyl) doxorubicin |
| 0 | CN | COCH$_2$OH | —OH,=O | 3'deamino-3'-(5''-keto-3''-cyano-4''-morpholinyl) doxorubicin |
| 0 | CN | COCH$_3$ | —O— | 3'-deamino-5'',4'anhydro-3'-(5''-hydroxy-3''-cyano-4''-morpholinyl) daunorubicin |
| 0 | CN | COCH$_3$ | —OH,—CN | 3'-deamino-3'-(3'', 5''-dicyano-4''-morpholinyl) daunorubicin |
| 0 | CN | COCH$_3$ | —OH,—OH | 3'-deamino-3'-(5''hydroxy-3''-cyano-4''-morpholinyl) daunorubicin |
| 0 | CN | COCH$_3$ | —OH,=O | 3'deamino-3'-(5''-keto-3''-cyano-4''-morpholinyl) daunorubicin |

Five of these materials are preferred because of their excellent activity as antitumor agents. These are 3'-deamino-3'-(3''-cyano-4''-morpholinyl)doxorubicin;

3'-deamino-3'-(3''-cyano-4''-morpholinyl)-13-dihydrodoxorubicin;

3'-deamino-3'-(3''-cyano-4''-morpholinyl)-daunorubicin;

3'-deamino-3'-(3''-cyano-4''-morpholinyl)-13-dihydrodaunorubicin; and

3'-deamino-3'-(4''-morpholinyl)-5-iminodoxorubicin.

The first of these five materials is the most preferred material.

The first four compounds of the invention listed in Table I can be the free bases shown in Table I or they can be pharmaceutically-acceptable acid addition salts of these bases. The acid addition salts offer the advantage of being soluble in water and aqueous mixed solvents such as water-alkanols or water-alkandiols. Examples of these mixed solvents are water-propylene glycol, water-ethanol, water-ethylene glycol, saline, various other aqueous injectable media, and the like. The free bases are soluble in less polar organic solvents such as choroform, methylene chloride, mixed chloroform-methanol solvents, and the like. They may also be used as suspensions.

The salts are the acid addition products of the free bases with a pharmaceutically acceptable acid. A "pharmaceutically-acceptable" acid is one which is nontoxic and generally employed in pharmaceutical products. Examples of these acids are inorganic acids such as hydrochloric, hydrobromic, sulfuric and phosphoric acids, and organic acids such as the carboxylic acids, e.g. acetic, glycolic, maleic, malic, hydroxymaleic, tartaric, citric, and salicylic acids and the organosulfonic acids, e.g. methanesulfonic and p-toluenesulfonic acid. Mixtures of two or more acids may be used as may mixtures of one or more free base plus one or more acid addition salt. For reasons of simplicity and ready solubility, the hydrochloric acid and hydrobromic acid addition salts are preferred.

The compounds of the invention may contain one or more chiral centers wherein the configuration is unspecified, in addition to the chiral centers in the saturated ring of dauno- or doxorubicin which have the noted configurations. Accordingly, the compounds of the invention may exist in diastereomeric forms. Such diastereomers may, of course, be separated using conventional techniques for separations of compounds in general, such as chromatography, selective crystallization and the like. The invention includes all such individual diastereomers, as well as mixtures thereof.

Those compounds of the invention wherein A is CN and Z is O do not, apparently, form acid addition salts, as the electron withdrawing effect of the cyano group destroys the basicity of the morpholino nitrogen. Thus the pharmaceutically acceptable acid addition salts claimed herein refer to salts of those embodiments wherein Z is NH (and are thus capable of forming salts using this more remote ring nitrogen) or wherein A and B are H.

As previously noted, these compounds can also be present as derivatives. These derivatives are formed so as to increase the solubility of the compounds or so as to vary other physical properties of the compounds.

Preparation

The compounds of the invention can be prepared by the following general route:

First, commercially available daunorubicin or doxorubicin (as an acid addition salt) is caused to react under reductive alkylation conditions with 2,2'-oxydiacetaldehyde

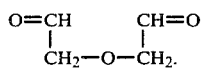

This alkylation yields a mixed product containing four principal components.

In the case of daunorubicin these components are;
3'-deamino-3'-(4''-morpholinyl)daunorubicin,
3'-deamino-3'-(4''-morpholinyl)-13-dihydrodaunorubicin,
3'-deamino-3'-(3''-cyano-4''-morpholinyl)daunorubicin, and
3'-deamino-3'-(3''-cyano-4''-morpholinyl)-13-dihydrodaunorubicin.

In the case of doxorubicin the reaction product contains;
3'-deamino-3'-(4''-morpholinyl)doxorubicin,
3'-deamino-3'-(4''-morpholinyl)-13-dihydrodoxorubicin,
3'-deamino-3'-(3''-cyano-4''-morpholinyl)doxorubicin, and
3'-deamino-3'-(3''-cyano-4''-morpholinyl)-13-dihydrodoxorubicin.

2,2'-oxydiacetaldehyde can be formed by acid hydrolysis of 2,2'-oxydiacetaldehyde bis(diethyl acetal)

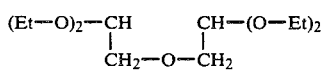

by the method of Field, et al's Belgian Pat. No. 655,436 or by cleavage of 1,4-anhydroerythritol

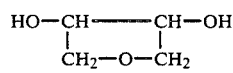

by the method of Barry, et al, *Carbohydrate Research*, 7, 299 (1968) and Greenberg, et al, *Carbohydrate Research*, 35, 195 (1974).

The reductive alkylation can be carried out using an excess of the dialdehyde in a mixed aqueous—polar organic medium, such as water—acetonitrile, generally at a pH of about 7 in the presence a reducing agent such as an alkali metal cyanoborohydride e.g. sodium or potassium cyanoborohydride. This is a relatively facile reaction which can usually be completed in an hour or less at room temperature. The reductive alkylation is illustrated in the Examples and is also shown in previously incorporated U.S. Pat. No. 4,301,277 and *J. Medicinal Chem.*, 25, pp. 18–24 (1982).

For those compounds wherein B is not hydrogen—i.e. is —OH, or —CN, or, combined with the co-carbon substituted H is =O, or combined with R' is —O—, the reaction is carried out as above, but with NaCN present in the reaction mixture rather than the reducing agent.

This procedure is exemplified in Example 12.

The work-up of the mixed reaction product may be carried out by any method that effects the desired isolation and separation. Acid extraction of the reaction product is effective to separate the acid-extractable non-cyano-substituted materials from the acid-insoluble cyano-substituted materials. The resulting pairs of materials can then be separated into individual compounds by various chromatography methods such as preparative layer chromatography, column chromatography, or preparative high performance liquid chromatography.

The 5-imino compounds can be easily and directly prepared from the isolated 5-oxo compounds using the method disclosed in the above-incorporated *J. Medicinal Chem*, 24, pp. 669 (1981) article. In this method the 5-oxo materials are contacted with an excess of alcoholic ammonia at low to moderate temperatures such as from $-25°$ C. to $+25°$ C. for from about 0.5 to about 100 hours. In the case of 3'-deamino-3'-(4''-morpholinyl)doxorubicin and 3'-deamino-3'-(3''-cyano-4''-morpholinyl)doxorubicin, it is necessary to block the hydroxyl on the 14 carbon before the ammonia treatment. Any mild acid-labile protecting group can be used. Because of its wide use in pharmaceutical chemistry, methoxy-trityl is a preferred protecting group. The trityl functionality can be introduced by treating 3'-deamino-3'-(4''-morpholinyl)doxorubicin or 3'-deamino-3'-(3''-cyano-4''-morpholinyl)doxorubicin with excess p-anisyl chlorodiphenylmethane at room temperature or the like. After the reaction with ammonia is complete, the 14-hydroxyl can be regenerated by contact with acid such as acetic acid or cold aqueous trifluoroacetic acid.

Derivatives and Analogues

In addition, the present invention provides derivatives and analogues of the foregoing 12 primary compounds. As shown in General Formula II, these derivatives can includes one or more of the following modifications of the primary compounds.

a. one or more of any hydroxyls present in R can be present as esters of 2 to 7 carbon organic acids, including alkanoic acids, oxyalkanoic acids, hydroxyalkanoic acids, and benzoic acid. This modification can give rise to R groups such as shown in Table II.

TABLE II

| Acid | Ester R's<br>Ester R |
|---|---|
| Acetic acid | $-CO-CH_2-O-COCH_3$ |
| | $-CH(OCOCH_3)-CH_2-O-COCH_3$ |
| | $-CH(OCOCH_3)-CH_2OH$ |
| | $-CH(OCOCH_3)-CH_3$ |
| Propionic acid | $-CO-CH_2-O-COC_2H_5$ |
| | $-CH(OCOC_2H_5)-CH_2-O-COC_2H_5$ |
| | $-CH(OCOC_2H_5)-CH_3$ |
| Glycolic acid | $-CO-CH_2-O-COCH_2OH$ |
| | $-CH(OCOCH_2OH)-CH_2-OCOCH_2OH$ |
| | $-CH(OCOCH_2OH)-CH_3$ |
| Benzoic acid | $-CO-CH_2-O-COC_6H_5$ |
| | $-CH(OCOC_6H_5)-CH_2-OCOC_6H_5$ |
| | $-CH(OCOC_6H_5)-CH_3$ |
| More complex acids such as $HOOC-CH(OC_2H_5)_2$ | $-CO-CH_2-O-COCH(OC_2H_5)_2$<br>etc. |

Such esters of doxorubicin described [Arcamone, et al, *J. Medicinal Chem.*, 17, 335(1974); Maral, et al, French Pat. No. 848,219 (May 10, 1977)] can be readily converted by the herein described reductive alkylation method to the corresponding ester derivatives of compounds of this invention.

b. One or more of any hydroxyls present in R can be present as ethers—particularly 1 to 6 carbon alkyl ethers or about 6 or 7 carbon aryl ethers. Representative "ether" R units are shown in Table III.

TABLE III

| | Ether R's |
|---|---|
| Methyl ether | $-CO-CH_2-OCH_3$ |
| | $-CH(OH)-CH_2-OCH_3$ |
| Ethyl ether | $-CO-CH_2-OC_2H_5$ |
| | $-CH(OH)-CH_2-OC_2H_5$ |
| Butyl ether | $-CO-CH_2OC_4H_9$ |
| Phenyl ether | $-CO-CH_2-O-C_6H_5$ |
| | $-CH(OH)-CH_2-OC_6H_5$ |

Such 14-ethers of doxorubicin have been described [Masi, et al, *Il Farmaco, Ed. Sci.*, 34, 907 (1979)] and can be used as starting materials in the reductive alkylation method of this invention.

c. The substituents of the 4' carbon in the "sugar" ring can be modified. The 4'-O-methyl derivatives (in the sugar unit) of doxorubicin and daunorubicin are readily obtained [Cassinelli, *J. Medicinal Chem.*, 22, 121 (1979)] and converted to compounds of this invention. Other known structural changes at the 4'-position of the sugar unit are the 4'-deoxy (no OH) and 4'-epi (OH up) derivatives of doxorubicin and daunorubicin (Suarato, et al, *Carbohydrate Res.* 98, c1 (1981)) which show promising pharmaceutical properties. These compounds are readily converted by the reductive alkylation process to the corresponding compounds of this invention.

d. The 4-demethoxy analogues of doxorubicin and daunorubicin (no CH$_3$O in A-ring of the aglycone) are readily obtained [Arcamone, et al, *Cancer Test Rpts.*, 60, 829 (1976); Arcamone, et al, German Pat. No. 2,652,391 (May 26, 1977)] and converted to compounds of this invention.

e. Carbonyl groups

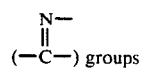

in the R units of daunorubicin and doxorubicin can be readily converted to

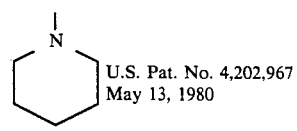 groups by the common methods for converting ketones to oximes, hydrazones, and other ketimines. Table IV lists representative ketimine R's

TABLE IV

Ketimine R's $-C(NOH)-CH_2OH$
$-C(NOH)-CH_3$
$-C(NOCH_3)-CH_2OH$
$-C(NOCH_3)-CH_3$
$-C(NNHCOC_6H_5)-CH_2OH$
$-C(NNHCOC_6H_5)-CH_3$
$-C(NNHCONH_2)CH_2OH$
$-C(NNHCONH_2)-CH_3$ and the like.

These 13-ketimine R materials can be readily converted to compounds of this invention by the above-described reductive alkylation.

f. The R unit can be simplified to eliminate the carbonyl and give rise to the simple hydroxyl R units shown in Table V.

TABLE V

Simplified R's $-OH$
$-CH_2OH$
$-C_2H_4OH$

These daunorubicin and doxorubicin materials are shown in Penco et al, German Pat. No. 27 57 057 July 7, 1978 and Penco et al, *J. Antibiotics,* 30:764 (1977) and are converted to compounds of this invention by reductive alkylation.

g. 2-Cyanopiperidino (Z=CH$_2$) and 2-Cyano-4-methoxypiperidino (Z=CHOCH$_3$) (Formula II). The piperidino derivatives of daunorubicin and doxorubicin have been described in U.S. patents.

U.S. Pat. No. 4,202,967
May 13, 1980

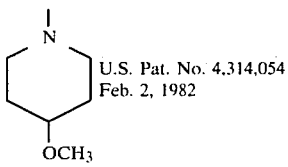

U.S. Pat. No. 4,314,054
Feb. 2, 1982

The corresponding 2-cyano-1-piperidinyl derivatives can be synthesized by converting the above compounds with meta-chloroperbenzoic acid in dichloromethane solution to the N-oxides, and rearrangement of the N-oxides with trifluoroacetic anhydride in the presence of cyanide ion (Polonovski-Potier-Husson).

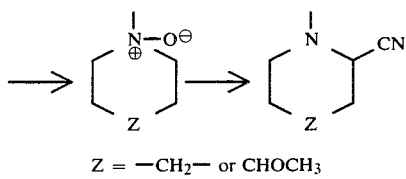

Z = —CH$_2$— or CHOCH$_3$

When the reductive alkylation procedure of this invention is carried out on daunorubicin, except that 2,2'-thiobisacetaldehyde (O=CHCH$_2$SCH$_2$CH=O; *Carbohydrate Res.*, 110, 195(1982)) is used in place of 2,2'-oxybisacetaldehyde, and the pH is weakly acidic (pH 6 instead of pH 7.2), the thiomorpholino derivative (A=H) (Formula I) of daunorubicin is obtained. This product is as active vs mouse leukemia P388 (T/C=169%) as doxorubicin (T/C=160%), although a higher dose is required (50 mg/kg instead of 8 mg/kg). Similarly, the thiomorpholino derivative of doxorubicin is formed when doxorubicin is used in this reaction.

The neutral product fraction from these reactions, which remins in the organic layer after extraction with aqueous acid to remove the thiomorpholino derivative as the water soluble acid salt, contains the corresponding 3-cyano-1-thio-4-morpholinyl derivatives (A=CN) of daunorubicin and doxorubicin.

All of the above referenced disclosures of derivitization methods are incorporated herein by reference.

This invention will be further shown by the following Examples. These are presented to illustrate the invention and are not to be construed as limiting the invention's scope.

EXAMPLE 1

Preparation, isolation and identification of 3'-deamino-3'-(3"-cyano-4"-morpholinyl)daunorubicin A. Following the method for preparing -3'-deamino-3'-morpholinodaunorubicin hydrobromide shown in Mosher, et al, *J. Medicinal Chem.*, 25, pp. 18–24 (1982) a crude reaction product containing 3'-deamino-3'-(4"-morpholinyl)daunorubicin, 3'-deamino-3'-(4"-morpholinyl)-13-dihydrodaunorubicin, 3'-deamino-3'-(3"-cyano-4"-morpholinyl)daunorubicin, and 3'-deamino-3'-(3"-cyano-4"-morpholinyl)-13-dihydrodaunorubicin was prepared. (This article is incorporated by reference.) The crude material was extracted with CHCl$_3$ as noted therein to remove the four primary products into the CHCl$_3$ phase. Exhaustive extraction of the CHCl$_3$ phase with 0.01N HCl removed the two basic morpholino products, as described in the reference. The neutral product-rich CHCl$_3$ was washed with NaHCO$_3$ solution, dried and evaporated. Samples were dissolved in 4:1 CHCl$_3$.CH$_3$OH and placed on a Waters Radial-Pak C-18 high performance liquid chromatography column, and eluted with 2 mL/minute of a 65:35 0.05M pH4 citrate buffer:CH$_3$CN eluent. One material (usually 19–24% of total) eluted at 6.1–6.8 minutes while another material (usually 26–27%) eluted at 11.9 minutes. Detection was by UV at 254 nm. As will be shown, the 6.1–6.8 minute material was 3'-deamino-3'-(3"-cyano-4"-morpholinyl)-13-dihydrodaunorubicin and the 11.9 minute material was 3'-deamino-3'-(3"-cyano-4"-morpholinyl)daunorubicin.

B. On a larger scale, 5.41 g of the solid byproduct was dissolved in 500 mL of 9:1 CHCl$_3$—CH$_3$OH. This solution was washed with 0.01N HCl (3×100 mL), H$_2$O (1×100 mL) and dilute NaHCO$_3$ (1×100 mL). The organic phase was dried, evaporated to dryness and the residue was vacuum dried at 0.1 mm and room temperature to give 5.10 g of glassy residue. The aqueous phase was retained, also.

C. The glassy residue of Part B, 5.09 g, was dissolved in 50 mL of 4:1 CH$_2$Cl$_2$—CH$_3$OH. The solution was stirred while 30 mL of CH$_3$CN was added dropwise. The turbid solution which resulted was evaporated to dryness to afford a semisolid residue which was triturated with 200 mL of CH$_3$CN in the dark. The insoluble solid was collected and triturated a second time with 100 mL of CH$_3$CN. The liquid phases of the two triturations contained the desired product. They were evaporated to give 2.23 g of semi-solid residue.

D. The semisolid residue of Part C was dissolved in 5 mL of CH$_2$Cl$_2$ and applied on a 3.1 cm o.d ×59 cm column of CH$_2$Cl-washed 200-325 mesh Mallinckrodt Silic AR CC-7 silica gel. The column was eluted with CH$_2$Cl$_2$ (500 mL) and then CH$_2$Cl$_2$—CH$_3$OH (99:1, 1500 mL; 98:2, 1000 mL; 97:3, 1500 mL; 90:10, 500 mL). After collection (10 mL fractions, monitored by TLC) of 2550 mL of initial eluate, a 190 mL fraction was evaporated to yield 0.48 g of product. The primary component was determined by comparative high performance liquid chromatography and thin layer chromatography to be identical to a material later proven to be 3'-deamino-3'-(3"-cyano-4"-morpholinyl)daunorubicin.

E. A 0.35 g sample of the material of Part D was further purified first in the dark on five 2 mm×20×20 cm silica gel plates with two CH$_2$Cl$_2$—CH$_3$OH 29:1 developments. A center band containing 65% of the applied weight of sample was cut out, eluted, filtered and evaporated to dryness.

F. The product of Part E, together with other equivalently purified materials recovered from chromatography flanking zones, (0.18 g) was given a final purification on a 1.1 cm o.d.×27 cm column of 200–400 mesh silica gel. The column was eluted with CH$_2$Cl$_2$—EtOAc (80:20, 30 mL; 60:40, 30 mL; 40:60, 30 mL; 20:80, 30 mL) and then EtOAc (175 mL). After collection (2 mL fractions. monitored by TLC) of 162 mL of initial eluate, an 88 mL fraction was collected and evaporated to afford 0.15 g of product.

Elemental analysis of this pure material verified the structure to be 3'-deamino-3'-(3"-cyano-4"-morpholinyl)daunorubicin as did 360 MHz NMR, UV, IR and mass spectroscopy.

The occurrence of this product as a diastereoisomeric mixture was indicated by HPLC and 360 MHz NMR analysis. HPLC analysis on a Waters Radial-Pak C-18 column with 0.05M pH 4 citrate buffer-CH$_3$CN (60:40) at 2 mL/minute showed two closely spaced peaks (at 9.6 minutes and 10.2 minutes) in the ratio 53:44. The 360 MHz NMR spectrum of this material exhibited two resonances for the 6-OH, 11-OH, 1-H, 2-H, 3-H, 1'-H, 7-H, 9-OH, 10A-H, 14-H$_3$ and 6-H$_3$ protons.

360 MHz NMR CDCl$_3$ ∫ 13.99, 13.98 (2s, 6-OH), 13.25, 13.24 (2s, 11-OH), 8.02, 8.00 (2d, 1-H), 7.79, 7.77 (2t, 2-H), 7.40, 7.38 (2d, 3-H), 5.59, 5.56 (2d, 1'-H), 5.29, 5.26 (2bs, 7-H), 4.47*, 4.34* )(2s, 9-OH), 4.08 (s, OCH$_3$), 3.97–4.07 (m, 2" B-H, 5'-H), 3.92 (t, J=12 Hz 3"-H), 3.74 (m, 6"A-H, 6"B-H), 3.68 (bs, 4'H), 3.58 (t, J=12 Hz, 2"A-H), 3.20 (d, J=19 Hz, 10B-H), 2.91, 2.90 (2d, J=19 Hz, 10A-H) 2.75–2.95 (m, 3'-H), 2.68 (m, 5"-H$_2$), 2.43, 2.42 (2s, 14-H$_3$), 2.35 (m, 8B-H), 2.13 (m, 8A-H), 1.70–2.0 (m, 2'-H$_2$), 1.86* (s, 4'-OH, H$_2$O), 1.37, 1.36 (2d, J=6.4 Hz), 6-H$_3$) *
*exchangeable with D$_2$O*

Mass Spectrum: [as the trimethylsilyl (TMS) derivatives], m/e 910 [M(TMS)$_4$], 895 [M(TMS)$_4$-Me], 883 [M(TMS)$_4$-HCN], 838 [M(TMS)$_3$], 823 [M(TMS)$_3$-Me], 811 [M(TMS)$_3$-HCN], MS at 70 ev. showed a base peak (HCN) at m/e 27.

EXAMPLE 2

Isolation of 3'-deamino-3'-(3"-cyano-4"-morpholinyl)-13-dihydrodaunorubicin

In Example 1, Part D, a mixture of 3'-deamino-3'-(3"-cyano-4"-morpholinyl)daunorubicin and 3'-deamino-3'-(3"-cyano-4"-morpholinyl)-13-dihydrodaunorubicin was chromatographed and a series of fractions were taken. After collection of 3460 mL of eluent a 430 mL fraction containing 12.5% of the initially charged material as essentially a single compound was collected and evaporated. The compound of this fraction was determined by HPLC to be identical to a material previously characterized by NMR and mass spectroscopy to be 3'-deamino-3'-(3"-cyano-4"-morpholinyl)-13-dihydrodaunorubicin. This material could be purified essentially by the methods shown in Example 1, Parts E and F to yield essentially pure 3'-deamino-3'-(3"-cyano-4"-morpholinyl)-13-dihydrodaunorubicin.

EXAMPLE 3

Isolation of 3'-deamino-3'-(4"-morpholinyl)-daunorubicin and 3'-deamino-3'-(4"-morpholinyl)-13-dihydrodaunorubicin In Example 1, Parts A and B, the 0.01N HCl phase containing 3'-deamino-3'-(4"-morpholinyl)daunoubicin and 3'-deamino-3'-(4"-morpholinyl)-13-dihydrodaunorubicin was isolated. This aqueous phase contained about 40% of the charged material. This aqueous phase was then worked up using the method shown in the previously-incorporated *J. Medicinal Chem.*, 25, reference to yield 3'-deamino-3'-(4"-morpholinyl)-daunorubicin and 3'-deamino-3'-(4"-morpholinyl)-13-dihydrodaunorubicin as separate isolated compounds.

EXAMPLE 4

Preparation and isolation of 3'-deamino-3'-(3"-cyano-4"-morpholinyl)doxorubicin and 3'-deamino-3'-(3"-cyano-4"-morpholinyl)-13-dihydrodoxorubicin A. In a reaction analogous to that shown in the *J. Medicinal Chem.*, 25 article, to a stirred solution of 6.25 g (60.0 mmol) of 1,4-anhydroerythritol,

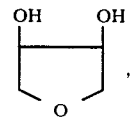

in 75 mL of H$_2$O cooled in a water bath at 15°–20° C. was added 6.42 g (30.0 mmol) of sodium metaperiodate. The resulting clear solution was stirred at room temperature for 17 hours. The solution pH was adjusted from 4.0 to 7.3 with NaHCO$_3$ and then diluted with stirring with 75 mL of CH$_3$CN. A precipitate formed. The mixture was stirred and 0.126 g (2.0 mmol) of NaBH$_3$CN in 5 mL of 1:1 (vol) CH$_3$CN-H$_2$O was added. To this mixture was then added 1.16 g (2.0 mmol) of doxorubicin hydrochloride in 30 mL of 1:1 CH$_3$CN-H$_2$O. After 10 minutes, the reaction mixture was diluted with 50 mL of dilute NaHCO$_3$ and extracted thrice with 50 mL portions of CHCl$_3$. This crude extract contained 3'-deamino-3'-(4"-morpholinyl)doxorubicin, 3'-deamino-3'-(4"-morpholinyl)-13-dihydrodoxorubicin, 3'-deamino-3'-(3"-cyano-4"-morpholinyl)doxorubicin and 3'-deamino-3'-(3"-cyano-4"-morpholinyl)-13-dihydrodoxorubicin. Combined extracts were extracted with 0.1N acetic acid (5×25 mL) and then with H$_2$O and washed with dilute NaHCO$_3$ and saturated aqueous NaCl. The acidic aqueous phase was retained. The chloroform phase was dried over Na$_2$SO$_4$, filtered through Celite TM diatomaceous earth and concentrated to yield a residue. This residue was dissolved in 25 mL of CHCl$_3$ and solvent re-evaporated under vacuum at room temperature. This afforded 0.518 g (40%) of a dark red foamed glass.

B. A sample of the foamed glass of Part A was dissolved in CH$_3$CN and injected into a Waters Radial-Pak C-18 high performance liquid chromatography column and eluted with pH 4.0 0.05M citrate buffer-CH$_3$CN 55:45 at 2 mL/minute. The elution of compounds was detected at 254 nm. At 2.3 minutes a material identified as 3'-deamino-3'-(3"-cyano-4"-morpholinyl)-13-dihydrodoxorubicin came off in 13% yield (based on injection mixture) and at 3.8 minutes, 3'-deamino-3'-(3"-cyano-4"-morpholinyl)doxorubicin came off in 69% yield. Other similar pooled products were obtained and separated by HPLC.

C. The isolation of 3'-Deamino-3'-(3"-cyano-4"-morpholinyl)doxorubicin and 3'-Deamino-3'-(3"-cyano-4"-morpholinyl)-13-dihydoxorubicin was subsequently repeated as follows:

A 0.424 g sample of the foamed glass of Part A was dissolved in 1.5 mL of CH$_2$Cl$_2$ and applied on a 1.5×35.5 cm column of CH$_2$Cl$_2$-washed 200–400 mesh Bio-Sil A Silica gel. The column was eluted with CH$_2$Cl$_2$ (50 mL) and then CH$_2$Cl$_2$-CH$_3$OH (99:1, 150 mL; 98:2, 150 mL; 97:3, 300 mL; 95:5, 100 mL and 90:10, 300 mL). After collection of 445 mL of initial eluate, an 80 mL fraction was evaporated to yield 0.217 g of product. This material was combined with 0.039 g of purified product from an earlier preparation and the mixture was dissolved in 2 mL of $CH_2Cl_2$, diluted with 10 mL of $CH_3OH$ and evaporated to dryness. Trituration of this residue with 5 mL of $CH_3OH$ afforded 0.218 g of 3'-deamino-3'-(3''-cyano-4''-morpholinyl)doxorubicin.

HPLC and 400 MHz NMR analysis indicated this product was a diastereoisomeric mixture. HPLC analysis on a Waters Radial-Pak C-18 column with 0.05M pH 4 citrate buffer-$CH_3CN$ (65:35) at 2 mL/minute showed two closely spaced peaks (at 14.4 minutes and 15.7 minutes) in the ratio 58:39. The 400 MHz spectrum of this material exhibited two resonances for the 1-H, 2-H, 3-H, 1'-H, 7-H, 14-$H_2$, 9-OH, $OCH_3$, 10A-H and 6'-$H_3$ protons.

400 MHz NMR $CDCl_3$ δ 14.02 (s, 6-OH), 13.26 (s, 11-OH), 8.05, 8.04, (2d, 1-H), 7.80, 7.79 (2t, 2-H), 7.41, 7.40 (2d, 3-H), 5.61, 5.57 (2d, 1'-H), 5.34, 5.30 (2m, 7-H), 4.79, 4.78 (2s, 14-$H_2$), 4.54, 4.42 (2s, 9-OH), 4.11, 4.10 (2s, $OCH_3$), 4.05 (m, 5'-H), 3.97 (m, 2''B-H, 3''-H, 6''B-H), 3.71 (m, 4'-H, 6''A-H), 3.58 (t, 2''A-H), 3.30 (d, J=19 Hz, 10B-H), 3.07, 3.06 (2d, 10A-H), 3.03 (m, 3'-H), 2.69 (m, 5''-$H_2$), 2.38 (m, 8B-H), 2.22 (m, 8A-H), 1.84 (m, 2'-$H_2$), 1.61 (s, $H_2O$), 1.40, 1.39 (2d, J=6.5 Hz, 6'-$H_3$).

UV-Vis ($CH_3OH$) max 234 nm (ε 40,100), 252 (27,700), 289 (9,420), 478 (13,000), 495 (12,900), 530 (7,190). Mass spectrum [as the trimethylsilyl (TMS) derivative], m/e 899 M(TMS)$_4$-HCN.

| | C | H | N |
|---|---|---|---|
| Calcd for $C_{32}H_{34}N_2O_{12}.2H_2O$ | 56.97 | 5.68 | 4.15 |
| Found | 57.07 | 5.37 | 4.17 |

Further elution of the above column gave 0.041 g of 3'-deamino-3'-(3''-cyano-4''-morpholinyl)-13-dihydrodoxorubicin. UV-Vis ($CH_3OH$) max 234 nm (ε 37,400), 252 (28,000), 289 (9,390), 475 (12,700), 496 (12,800), 530 (7,410). Mass spectrum [as the trimethylsilyl (TMS) derivative], m/e 985 M(TMS)$_5$-$CH_3$, 973 M(TMS)$_5$-HCN

| | C | H | N |
|---|---|---|---|
| Calcd for $C_{32}H_{36}N_2O_{12}.1\frac{1}{2}H_2O$ | 57.57 | 5.89 | 4.20 |
| Found | 57.35 | 5.94 | 3.82 |

EXAMPLE 5

Isolation of 3'-deamino-3'-(4''-morpholinyl)doxorubicin and 3'-deamino-3'-(4''-morpholinyl)-13-dihydrodoxorubicin A. The acidic aqueous phase obtained in Part A of Example 4 was basified with $NaHCO_3$ and extracted with $CHCl_3$. The $CHCl_3$ phase was washed with saturated NaCl, dried over $Na_2SO_4$, filtered through Celite ™, concentrated and dried to give 0.828 g of a red foam which by HPLC, 90 MHz NMR, 300 MHz NMR, UV-Vis spectroscopy and mass spectroscopy was shown to contain two primary components, 3'-deamino-3'-(4''-morpholinyl)doxorubicin and 3'-deamino-3'-(4''-morpholinyl)-13-dihydrodoxorubicin.

B. A pool of 0.98 g of the foamed glass such as was prepared in Part A was made up. This material was dissolved in 3 mL of $CH_2Cl_2$ and chromatographed on a 2.2×33 cm column of silica gel. The column was eluted with $CH_2Cl_2$ (50 mL) and then $CH_2Cl_2$-$CH_3OH$ (99:1, 300 mL; 98:2, 300 mL; 97:3, 900 mL and 90:10, 700 mL). After collecting an initial 1170 mL of eluent, a 490 mL fraction was isolated and evaporated to give a residue. This residue contained 45% of the charged sample and by HPLC was seen to be essentially pure (99+%) 3'-deamino-3'-(4''-morpholinyl)doxorubicin.

90 MHz NMR $CDCl_3$ δ 13.88 (s, 6-OH), 13.07 (s, 11-OH), 7.90 (d, J=8 Hz, 1-H), 7.72 (t, J=8 Hz, 2-H), 7.38 (d, J=8 Hz, 3-H), 5.51 (bs, 1'-H), 5.20 (bs, 7-H), 4.75 (s, 14-$H_2$), 4.68 (s, 9-OH), 4.07 (s, $OCH_3$), 3.98 (m, 5'-H), 3.67 (m, 4'-H, 2''-$H_2$, 6''-$H_2$), 3.09 (d, J=19 Hz, 10B-H), 2.83 (d, J=19 Hz, 10A-H), 2.80–3.20 (m, 3'-H), 2.50–3.00 (bs, 4'-OH, 14-OH), 1.95–2.65 (m, 8-$H_2$, 3''-$H_2$, 5''-$H_2$), 1.80 (m, 2'-$H_2$), 1.38 (d, J=6.5 Hz, 6'-$H_3$). Mass spectrum [as the trimethylsilyl (TMS) derivatives], m/e 973 M(TMS)$_5$, 901 M(TMS)$_4$.

The free base was suspended in $H_2O$ and acidified to pH 4.4 with 0.1N HCl. The resultant solution was lyophilized and the product was dissolved in $CH_3OH$ and precipitated with 10 volumes of ether to afford the hydrochloride.

| | C | H | Cl$^-$ | N |
|---|---|---|---|---|
| Calcd for $C_{31}H_{35}NO_{12}.HCl.2H_2O$ | 54.27 | 5.88 | 5.17 | 2.04 |
| Found | 54.08 | 5.35 | 4.78 | 2.00 |

UV-Vis ($CH_3OH$) max 234 nm (ε 39,000), 252 (26,300), 290 (8,990), 480 (12,600), 495 (12,500), 530 (6,700).

A 190 mL fraction was taken followed by a 160 mL fraction. This latter fraction was evaporated and found to contain 19.5% of the charged material as 97% pure 3'-deamino-3'-(4''-morpholinyl)-13-dihydrodoxorubicin.

300 MHz NMR $CDCl_3$ δ 13.98, 13.96 (2s, 6-OH), 13.34, 13.32 (2s, 11-OH), 8.03 (d, 1-H), 7.79 (t, 2-H), 7.40 (d, 3-H), 5.56 (bs, 1'-H), 5.29 (bs, 7-H), 4.64, 4.59 (2s, 9-OH), 4.09 (s, $OCH_3$), 4.03 (m, 5'-H), 3.82–4.05 (m, 4'-H, 13-H), 3.68 (m, 2''-$H_2$, 6''-$H_2$, 14B-H), 3.54 (bs, 14A-H), 3.30 (m, 10B-H), 2.98 (bs, OH), 2.87 (bs, OH), 2.77 (m, 10A-H, 3'-H), 2.30–2.70 (m, 8B-H, 3''-$H_2$, 5''-$H_2$), 1.99 (m, 8A-H), 1.78 (m, 2'-$H_2$), 1.41 (d, 6'-$H_3$) Mass spectrum [as the trimethylsilyl (TMS) derivative]. m/e 975 M(TMS)$_5$.

EXAMPLE 6

Preparation of 3'-deamino-3'-(4''-morpholinyl)-5-iminodoxorubicin

A. To a solution of 0.396 g of 3'-deamino-3'-(4''-morpholinyl)doxorubicin prepared as shown in Example 5 in 5 mL of dry pyridine was added 0.990 g of p-anisyl chlorodiphenylmethane. The mixture was allowed to react at room temperature in the dark for about two days. The solution was cooled in ice water and 0.5 mL of $CH_3OH$ was added. The mixture was stirred for 2 hr and added to 50 mL of dilute $NaHCO_3$ and extracted with $CH_2Cl_2$. The extracts were concentrated to give a gummy residue which was dissolved in toluene, concentrated, dissolved in $CH_2Cl_2$ and precipitated by slowly adding 35°–60° petroleum ether. This precipitate was recovered, redissolved in $CH_2Cl_2$ and precipitated with 2:1 petroleum ether:diethyl ether to afford 14-O-p-anisyldiphenyl methyl-3'-deamino-3'-(4''-morpholinyl)- doxorubicin, (III), as an amorphous solid in 94% yield.

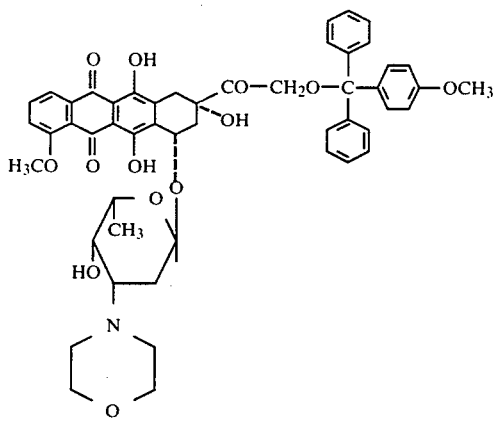

(III)

This material was identified by 90 MHz NMR in CDCl$_3$.

B. A solution of 0.532 g of 14-O-p-anisyldiphenyl methyl-3'-deamino-3'-(4''-morpholinyl)doxorubicin in 10 mL of CH$_2$Cl$_2$ was added to 30 mL of CH$_3$OH saturated with ammonia at 0° C. The mixture was stirred at 0° C. for an hour and then allowed to stand at 3° C. for 27 hours. Solvent in the reaction product was evaporated. The residue was dissolved in 4:1 CH$_2$Cl$_2$-CH$_3$OH and concentrated. This was repeated twice and the solid was dissolved in CH$_2$Cl$_2$, filtered through Celite TM, concentrated, dissolved in 1:2 CH$_2$Cl$_2$-CH$_3$OH and again concentrated and dried to yield 0.52 g (97%) of a violet residue.

C. The residue of Part B was dissolved in 2 mL of CH$_2$Cl$_2$ and applied on a 1.5×40 cm silica gel column and eluted with CH$_2$Cl$_2$ (50 mL) and then CH$_2$Cl$_2$-CH$_3$OH (99:1, 150 mL; 98:2, 150 mL; 97:3, 500 mL; 95:5, 100 mL; 93:7, 100 mL; and 90:10, 200 mL). Following 565 mL of eluent, a 335 mL fraction was separated, filtered and evaporated to contain 59.9% of the applied sample as a single material. This material was identified as 14-O-p-anisyldiphenylmethyl-3'-deamino-3'-(4''-morpholinyl)-5-iminodoxorubicin by 90 MHz NMR.

D. A 0.341 g sample of the product of Step C was dissolved in 20 mL of 80% acetic acid and the solution was stirred in the dark for seven hours. The solution was then diluted with 50 mL of water and extracted three times with CHCl$_3$. The aqueous phase contained the desired product and was lyophilized in the dark to give 0.294 g of solid. The solid was dissolved in 0.1N acetic acid. The solution was washed with CHCl$_3$ basified with NaHCO$_3$ and extracted with CHCl$_3$. The desired product went into the organic phase which was washed, dried, filtered and concentrated to give a residue. This residue was dissolved in CHCl$_3$-CH$_3$OH (1:10) concentrated and dried to give 0.228 g of 3'-deamino-3'-(4''-morpholinyl)-5-iminodoxorubicin. The material's identity was verified by 300 MHz NMR and elemental analysis.

EXAMPLE 7

Preparation of acid addition salt

The free base product of Example 6 was suspended in 20 mL of water. The mixture was stirred and 3.2 mL of 0.1N HCl was slowly added to give a pH of 4.5. The suspended solid gradually dissolved. The solution was lyophilized in the dark to give the acid addition salt 3'-deamino-3'-(4''-morpholinyl)-5-iminodoxorubicin hydrochloride in 97+% purity by HPLC analysis

|  | C | H | Cl$^-$ | N |
|---|---|---|---|---|
| Calcd for C$_{31}$H$_{36}$N$_2$O$_{11}$.HCl.2H$_2$O | 54.35 | 6.03 | 5.17 | 4.09 |
| Found | 54.20 | 5.96 | 4.33 | 4.03 |

EXAMPLE 8

Preparation and isolation of 3'-deamino-3'-(4''-morpholinyl)-5-imino-13-dihydrodoxorubicin A. A solution of 0.186 g of 3'-deamino-3'-(4''-morpholinyl)-13-dihydrodoxorubicin prepared as in Example 5 in 6 mL of 1:1 CH$_2$Cl$_2$-CH$_3$OH was added to 20 mL of CH$_3$OH saturated with ammonia at 0° C. The mixture was stirred for an hour and then stored at 3° C. for about 27 hours, concentrated and the residual product dissolved in CH$_2$Cl$_2$-CH$_3$OH (4:1) and concentrated thrice to completely remove ammonia. The resulting residue was purified by preparative thin layer chromatography on 2 mm×20 cm×20 cm silica gel plates using CHCl$_3$-CH$_3$OH 9:1 development. Bands containing essentially pure 3'-deamino-3'-(4''-morpholinyl)-5-imino-13-dihydrodoxorubicin were separated, eluted and the eluent dried to afford 0.139 g of the free base product as identified by 300 MHz NMR.

B. The free base of Part A was converted to the hydrochloride by the method of Example 7. By HPLC analysis, the hydrochloride was 97–98% pure.

|  | C | H | Cl$^-$ | N |
|---|---|---|---|---|
| Calcd for C$_{31}$H$_{38}$N$_2$O$_{11}$.HCl.2H$_2$O | 54.19 | 6.31 | 5.16 | 4.08 |
| Found | 54.17 | 5.95 | 4.88 | 3.87 |

EXAMPLE 9

Preparation of 3'-deamino-3'-(3''-cyano-4''-morpholinyl)-5-iminodaunorubicin

A solution of 0.031 g of 3'-deamino-3'-(3''-cyano-4''-morpholinyl)daunorubicin in 1.0 mL of CH$_2$Cl$_2$ was added to 5 mL of ammonia-saturated methanol at 0° C. The mixture was stirred for 30 minutes and then stored at 3° C. for 45 hours. The product of this reaction was evaporated to dryness to give a residue which was dissolved in 5 mL of 19:1 CHCl$_3$-CH$_3$OH and concentrated. This step was repeated. This residue was dissolved in CHCl$_3$-CH$_3$OH and applied to a 2 mm 20 cm×20 cm silica gel plate and developed using 9:1 CHCl$_3$-CH$_3$OH. The major band was eluted and analyzed. Mass spectroscopy verified the compound to be 3'-deamino-3'-(3''-cyano-4''-morpholinyl)-5-iminodaunorubicin.

EXAMPLE 10

The preparation of Example 6 was repeated using 3'-deamino-3'-(3''-cyano-4''-morpholinyl)doxorubicin prepared as in Example 4 as feed material in place of 3'-deamino-3'-(4''-morpholinyl)doxorubicin. The blocking-amination-deblocking isolation sequence of Example 6 is used to yield 3'-deamino-3'-(3''-cyano-4''-morpholinyl)-5-iminodoxorubicin as the final product.

In more detail, this preparation was as follows:

A. To a solution of 0.241 g of 3'-deamino-3'-(3"-cyano-4"-morpholinyl)doxorubicin prepared as shown in Example 4 in 4 mL of dry pyridine was added 0.587 g of p-anisylchlorodiphenylmethane. The solution was stirred at room temperature in the dark for 44 hr. The reaction mixture was cooled, diluted with 0.5 mL of $CH_3OH$, stirred at room temperature for 3 hr and then added to 50 mL of dilute $NaHCO_3$ and extracted with $CH_2Cl_2$. The extracts were concentrated, the residue was dissolved in 3 mL of $CH_2Cl_2$ and precipitated by slowly adding 40 mL of diethyl ether to afford 0.333 g (97%) of 14-O-p-anisyldiphenylmethyl-3"-deamino-3'-(3"-cyano-4"-morpholinyl)doxorubicin. 90 MHz NMR $CDCl_3$ δ 13.84 (s, 6-OH), 12.99 (s, 11-OH), 7.82 (d, 1-H), 6.70–7.75 (m, 2-H, 3-H, trityl-aryl), 5.42 (bs, 1'-H), 5.08 (bs, 7-H), 4.45 (bs, 2, 14-$H_2$), 4.19 (s, 9-OH), 4.00 (s, $OCH_3$), 3.79 (s, $OCH_3$), 3.30–4.15 (m, 4'-H, 5'-H, 2"-$H_2$, 3"-H, 6"-$H_2$), 1.60–3.10 (m, 2'-$H_2$, 8-$H_2$, 5"-$H_2$, 10-$H_2$, 3'-H), 1.13 (d, 6'-$H_3$).

B. A solution of 0.369 g of 14-O-p-anisyldiphenylmethyl-3'-deamino-3'-(3"-cyano-4"-morpholinyl)doxorubicin in 8 mL of $CH_2Cl_2$ was added to 25 mL of $CH_3OH$ saturated with ammonia at 0° C. The mixture was stirred at 0° C. for an hour and then allowed to stand at 3° C. for 26 hr. The reaction mixture was evaporated, to completely remove ammonia and yield 0.376 g of a violet residue.

C. The residue of Part B in 1.5 mL of $CH_2Cl_2$ was applied on a 1.5×28 cm (200–400 mesh) silica gel column and eluted with $CH_2Cl_2$ (50 mL) and then $CH_2Cl_2$-$CH_3OH$ (99:1, 200 mL; 98:2, 300 mL; 97:3, 100 mL; 95:5, 100 mL; and 90:10, 200 mL). After collection of 360 mL of initial eluate, a 125 mL fraction was evaporated to yield 0.203 g of 14-O-p-anisyldiphenylmethyl-3'-deamino-3'-(3"-cyano-4"-morpholinyl)-5-iminodoxorubicin.

D. A 0.158 g sample of the residue of Part C was cooled to 0° C. and dissolved in 8 mL of ice cold 50% trifluoroacetic acid. The solution was stirred at 0° C. for 2 min and then poured into 100 mL of ice water. The aqueous mixture was extracted with $CHCl_3$ (4×10 mL) and the combined extracts were washed with dilute $NaHCO_3$ and $H_2O$, dried over $Na_2SO_4$, filtered through Celite ™ and evaporated. The residue was dissolved in 3 mL of $CHCl_3$-$CH_3OH$ (4:1); the solution was stirred and 25 mL of ether was added dropwise. The resulting precipitate was collected to afford 0.093 g of 3'-deamino-3-(3"-cyano-4"-morpholinyl)-5-iminodoxorubicin.

HPLC and 300 MHz NMR analysis indicated this material was a diastereoisomeric mixture. HPLC analysis on a Waters Radial-Pak C-18 column with 0.05M pH 4 citrate buffer-$CH_3OH$ (40:60) showed peaks at 18.4 min and 25.0 min in the ratio 69:31. The 300 MHz spectrum of this product exhibited two resonances for the 1-H, 2-H, 3-H, 1'-H, 7-H, 14-$H_2$, 9-OH, $OCH_3$, 10A-H, and 6'-$H_3$ protons.

300 MHz NMR $CDCl_3$ δ 15.61 (s, 11-OH), 13.74 (d, 6-OH), 9.27 (d, NH), 8.21, 8.19 (2d, 1-H), 7.73, 7.72 (2t, 2-H), 7.33, 7.32 (2d, 3-H), 5.77, 5.72 (2d, 1'-H), 5.41, 5.38 (2m, 7-H), 4.79, 4.77 (2s, 14-$H_2$), 4.72, 4.66 (2s, 9-OH), 4.15, 4.14 (2s, $OCH_3$), 4.04 (m, 5'-H), 3.97 (m, 3"-H, 2"B-H), 3.75 (m, 6"-$H_2$, 4'-H), 3.59 (m, 2"A-H), 3.23 (d, 10B-H), 3.03 (m, 10A-H, 3'-H), 2.72 (m, 5"-$H_2$), 2.33 (m, 8B-H), 2.14 (m, 8A-H), 1.85 (m, 2'-$H_2$), 1.38, 1.37 (2d, 6'-$H_3$).

UV-Vis ($CH_3OH$) max 221 nm (ε 31,000), 252 (32,900), 307 (7,110), 520 sh (9.110), 551 (17,400), 592 (20,700). DCI-MS m/e 638 (M+H), 611 (M+H-HCN)

|  | C | H | N |
|---|---|---|---|
| Calcd for $C_{32}H_{35}N_3O_{11} \cdot H_2O$ | 58.62 | 5.69 | 6.41 |
| Found | 58.79 | 5.47 | 6.30 |

EXAMPLE 11

The preparation of Example 8 is repeated four times each time using an equivalent molar amount of a different starting material in place of 3'-deamino-3'-(4"-morpholinyl)-13-dihydrodoxorubicin. In the first repeat, 3'-deamino-3'-(3"-cyano-4"-morpholinyl)-13-dihydrodoxorubicin is used as feed material to give 3'-deamino-3'-(3"-cyano-4"-morpholinyl)-5-imino-13-dihydrodoxorubicin as final product. In the second repeat, 3'-deamino-3'-(4"-morpholinyl)daunorubicin is used as feed material to give 3'-deamino-3'-(4"-morpholinyl)-5-iminodaunorubicin as final product. In the third repeat 3'-deamino-3'-(4"-morpholinyl)-13-dihydrodaunorubicin is used as feed material to give 3'-deamino-3'-(4"-morpholinyl)-5-imino-13-dihydrodaunorubicin as final product. In the forth repeat 3'-deamino-3'-(3"-cyano-4"-morpholinyl)-13-dihydrodaunorubicin is used as feed material to give 3'-deamino-3'-(3"-cyano-4"-morpholinyl)-5-imino-13-dihydrodaunorubicin as final product.

EXAMPLE 12

Preparation of
3'-Deamino-3'-(3"-cyano-5'-oxo-4"-morpholinyl) daunorubicin (oxoMRD) and
3'-Deamino-5",4"-anhydro-3'(5"cyano-3"-hydroxy 4"-morpholinyl) daunorubicin (anhydroMRD) and
3'-Deamino-3'-(3",5"-dicyano-4"-morpholinyl) daunorubicin (diCNMRD)

An aqueous acetonitrile solution of daunorubicin hydrochloride (56 mg) was reacted with 15 eq of 2,2'-oxybisacetaldehyde (prepared in situ by sodium metaperiodate oxidation of 1,4-anhydroerythritol) and 10 eq of sodium cyanide (adjusted to pH 6.3 with AcOH) at room temperature for 1 hr. The reaction mixture was worked up using standard procedures and followed by preparative TLC to afford 3 major fractions: A (12 mg), B (9 mg) and C (12 mg). The fractions were characterized by HPLC, NMR and MS.

Fraction A was identified as a mixture of ~25% oxoMRD, ~29% anhydroMRD, and contained several HPLC peaks (~12%, ~5%, ~7%, and ~11%) which could be assigned to diCNMRD. EI-MS of Fraction A (as the TMS derivatives) showed, in addition to the TMS derivatives of the two majority components, m/e 920 diCNMRD+$TMS_4$-$CH_3$] and 848 [diCNMRD+$TMS_3$-$CH_3$]. NDCI-MS (Negative ion desorption chemical-ionization-MS) showed m/e 647 (diCNMRD), 636 (oxoMRD) and 620 (anhydroMRD).

Fraction B was identified by HPLC as 91% of a "fast TLC" isomer of (anhydroMRD) and 4% of a slow isomer of this compound. The NMR spectrum is similar to that of 3'-deamino-3'-(3"-cyano 4"-morpholinyl) daunorubicin except for a new resonance at 4.67δ (3"-H). DCI-MS of Fraction B gave m/e 621 anhydroMRD+H], 594 [anhydroMRD+H—HCN].

NDCI-MS gave m/e 620 (anhydroMRD) and 593 [anhydroMRD-HCN].

Fraction C was identified by HPLC as ~12% "fast TLC" isomer and ~76% "slow TLC" isomer of anhydroMRD. The NMR spectrum is compatible with the structure of anhydroMRD; the resonance at 4.60δ is assignable to 3"-H. DCI-MS of Fraction C gave m/e 621 [anhydroMRD-H]H] and 593 [anhydroMRD+H−HCN]- HCN]; NDCI-MS gave m/e 620 [anhydroMRD] and 593 [anhydroMRD-HCN]-HCN].

(Reductive alkylation of daunorubicin hydrochloride with 2,2'-oxybisacetaldehyde in the presence of sodium cyanoborohydride also yields small amounts of oxoMRD and anhydroMRD in addition to 3'-deamino-3'-(3"-cyano 4"-morpholinyl) daunorubicin and its analog wherein R=CHOHCH$_3$, and 3'-deamino-3'(4"-morpholinyl) daunorubicin and its analog wherein R=CHOHCH$_3$.

Purification of the neutral fraction from such a reductive alkylation reaction (see Example 1, Part A–D) by silica gel column chromatography in CH$_2$Cl$_2$-CH$_3$OH afforded a few percent of two diastereoisomers of anhydroMRD, which are chromatographically identical to anhydroMRD prepared from the sodium cyanide reaction of this Example.

Purification of another fraction from the above column by silica gel chromatography in CH$_2$Cl$_2$-EtOAc yielded a few percent of two diastereoisomers of oxoMRD which are chromatographically identical to oxoMRD prepared from the sodium cyanide reaction. For one of these disastereomers, HPLC indicated ~95% "fast TLC" oxoMRD. The NMR spectrum is similar to that of 3'-(3"-cyano 4"-morpholinyl) daunorubicin except for additional resonances at 5.30 and 4.68δ (6"B-H and 6"A-H) and the absence of 5"-H$_2$ resonance near 2.6. EI-MS (as the TMS derivatives) gave m/e 909 [oxoMRD+TMS$_4$−CH$_3$] and 894 [oxoMRD+TMS$_4$−2CH$_3$]. DCI-MS gave m/e 637 [OxoMRD+H], 610 [oxoMRD+H−HCN]. NDCI-MS gave m/e 636 [oxoMRD], and 609 [oxoMRD−HCN]. For the other diastereomer, HPLC indicated ~96% purity. The NMR spectrum is very similar to that of the fast TLC isomer of oxoMRD above. EI-MS, DCI-MS and NDCI-MS gave spectra nearly identical to those of the fast TLC isomer of oxoMRD above.

EXAMPLE 13

Preparation of 3'-deamino-5",4'-anhydro-3'(5"-cyano-3"-hydroxy 4"-morpholinyl) doxorubicin (anhydroMRA)

Purification of the neutral fraction prepared as described in Example 4, Parts A–C afforded a few percent of two diastereoisomers of anhydroMRA. HPLC indicated ~96% purity and a diastereoisomer ratio of 3:7. The NMR spectrum was similar to that of 3'-deamino-3'(3"-cyano 4"-morpholinyl) doxorubicin except for new resonances at δ4.65 and δ4.58 [3"-H of the two isomers of anhydroMRA] and the absence of 5"-H$_2$ resonance near 2.7. EI-MS (underivatized) gave m/e 27 (HCN); DCI-MS gave m/e 637 [anhydroMRA+H], and 610 [anhydroMRA+H−HCN].

Elemental analysis of the purified anhydroMRA gave:

| | C | H | N |
|---|---|---|---|
| Calcd for C$_{32}$H$_{32}$N$_2$O$_{12}$·½H$_2$O | 59.53 | 5.15 | 4.34 |
| Found | 59.34 | 5.17 | 4.29 |

EXAMPLE 14

The preparations of Examples 1–13 are repeated using in place of doxorubicin or daunorubicin as starting materials the range of derivitized doxorubicins and daunorubicins described and prepared as described herein in the section denominated "Derivatives and Analogues". These repeats give rise to the corresponding derivatives and analogues of the compounds of the invention.

The compounds of this invention have utility as mammalian antitumor agents. This activity is evidenced by in vivo and in vitro studies. In one in vivo test, conducted in accordance with the protocol described in *Cancer Chemotherapy Reports, National Cancer Institute*, 3, No. 2, Part 3, September, 1972, healthy mice were inoculated i.p. with Lymphocyte Leukemia P-388 ascitic fluid. The inoculated mice were then treated on days 5, 9 and 13 of the succeeding period with various amounts of compounds of the invention. As comparisons, other mice were untreated and additional mice were treated with daunorubicin, or doxorubicin; 3'-deamino-3'-(4"-morpholinyl)daunorubicin or 3'-deamino-3'-(4"-morpholinyl)-13-dihydrodaunorubicin of U.S. Pat. No. 4,301,277 or 3'-deamino-3'-(4-methoxy-1-piperidinyl)daunorubicin or its 13-dihydro equivalent shown in U.S. Pat. No. 4,314,054.

The average survival time of the various treated mice was determined and compared with that of the mice inoculated with the leukemia ascitic fluid but given no treatment with the test compounds. Presented in the following Table A are the data so obtained. The data are presented as % T/C values which are the survival time of the treated mice divided by the survival time of the controls multiplied by 100. Also given in Table A are the dosage levels of the various compounds which were observed to produce the best survival time improvements.

TABLE A

| Compound | NSC No.* | Activity vs Leukemia P-388 in Mice | | Leukemia L-1210 Cells | |
|---|---|---|---|---|---|
| | | Survival Time % T/C | Optimum Dose (q4d 5,9,13) mg/kg | Inhibition of Synthesis ED$_{50}$, μM | |
| | | | | DNA | RNA |
| 3'-deamino-3'-(3"-cyano-4"-morpholinyl) daunorubicin | 332,304 | 197 | 0.4 | 0.012 | 0.00 |
| 3'-deamino-3'-(3"-cyano-4"-morpholinyl)-13-dihydrodaunorubicin | 332,305 | 143 | 0.1 | 0.019 | 0.00 |
| 3'-deamino-3'-(3"-cyano-4"-morpholinyl)- | 357,704 | 187 | 0.075 | 0.003 | 0.00 |

TABLE A-continued

| Compound | NSC No.* | Activity vs Leukemia P-388 in Mice | | Leukemia L-1210 Cells Inhibition of Synthesis $ED_{50}, \mu M$ | |
|---|---|---|---|---|---|
| | | Survival Time % T/C | Optimum Dose (q4d 5,9,13) mg/kg | DNA | RNA |
| doxorubicin 3'-deamino-3'-(3''-cyano-4''-morpholinyl)-13-dihydrodoxorubicin | 360,291 | 150 | 0.2 | 0.021 | 0.00 |
| 3'-deamino-3'-(4''-morpholinyl)-13-dihydro-5-iminodoxorubicin | 355,465 | 161 | 50 | >100 | 24 |
| For comparison: | | | | | |
| daunorubicin | 82,151 | 130 | 8 | 0.66 | 0.33 |
| doxoubicin | 123,127 | 160 | 8 | 1.5 | 0.58 |
| 3'-deamino-3'-(4''-morpholinyl)daunorubicin | 327,451 | 166 | 0.2 | 0.76 | 0.10 |
| 3'-deamino-3'-(4''-morpholinyl)-13-dihydrodaunorubicin | 327,450 | 132 | 0.2 | 2.2 | 0.67 |
| 3-deamino-3'-(4''-methoxy-1''-piperidinyl)-daunorubicin | 334,353 | 199 | 6.25 | 0.63 | 0.12 |
| 3'-deamino-3'-(4'-methoxy-1-piperidinyl)-13-dihydrodaunorubicin | 334,354 | 199 | 12.5 | 0.58 | 0.08 |
| 3'-deamino-3'-(3''-cyano-5''-oxo-4''-morpholinyl)-doxorubicin, two diastereoisomers | — | — | — | 0.05 | 0.03 |
| | | | | 0.05 | 0.03 |
| 3'-deamino-4',5''-anhydro-(3''-cyano-5''-hydroxy-4''-morpholinyl) daunorubicin, two diastereoisomers | — | — | — | 1.95 | 0.84 |
| | | | | 0.42 | 0.23 |
| 3'-deamino-4',5''-anhydro-(3''-cyano-5''-hydroxy-4''-morpholinyl) doxorubicin, diastereoisomeric mixture | — | — | — | 1.7 | 0.48 |

*NSC No. = National Service Center of US National Cancer Institute registration number.

These results show that compounds of this invention have good to superior in vivo antitumor activity at low optimum dosages. Compound NSC 357704 showed an optimum dose level about 1/150th that required with the parent compound. Other materials of the invention show optimum dose levels far lower than daunorubicin and doxorubicin. This gives promise of providing an active antitumor agent with substantially decreased cardiotoxicity.

In vitro tests of 3'-deamino-3'-(3''-cyano-4''-morpholinyl)daunorubicin and 3'-deamino-3'-(3''-cyano-4''-morpholinyl)-13-dihydrodaunorubicin also showed the increased activity in this class of compounds. When these materials were tested as inhibitors of DNA and RNA synthesis in L 1210 Cells by the method described in G. Tong, W. W. Lee, D. R. Black and D. W. Henry, *J. Medicinal Chem,* 19, 395 (1976), they were active at doses that were as much as 600 times lower than the doses of daunorubicin, doxorubicin, or the previous analogues. They were also observed to be much more inhibitory toward RNA synthesis than toward DNA synthesis (ED 50 Ratio DNA/RNA = 10 to 11). It has been suggested by S. T. Crooke, et al, *Mol. Pharmacol.,* 14, 290 (1978) that such a ratio indicates Class II anthracyclines having improved therapeutic properties. These data are shown in Table A.

The data in Table A, showing increased antitumor potency with the morpholino structure and further increase in efficacy with the cyanomorpholino structure, typify activity with this class of compounds.

Additional tests were run to verify the biological activity of compounds of this invention. These were in vivo tests in mice against P-388 and L1210 leukemia and B-16 Melanoma carried out essentially by the method of the above-noted *Cancer Chemotherapy Reports,* 1972. Various dose schedules and I.P., I.V. and oral routes of administration were tested. These results are given in Table B.

TABLE B

| | Mouse Antitumor Efficacy at Optimum Dose % T/C (mg/kg) | | | | | | | | | |
|---|---|---|---|---|---|---|---|---|---|---|
| Compound NSC No. | 82151* | 123127* | 327451(4)* | 327450(1)* | 332304 | 332305 | 354646(2)* | 355277(3) | 357704 | 360291 |
| ip L1210 | | | | | | | | | | |
| d 1, ip q4d 1, 5,9,ip | | 168(5) | | | | | 152(0.05) | | 164(0.025) >164(0.0125) | 152(0.025) >128(0.05) |

TABLE B-continued

Mouse Antitumor Efficacy at Optimum Dose % T/C (mg/kg)

| Compound NSC No. | 82151* | 123127* | 327451(4)* | 327450(1)* | 332304 | 332305 | 354646(2)* | 355277(3) | 357704 | 360291 |
|---|---|---|---|---|---|---|---|---|---|---|
| qd 1-9, ip ip P388 | | 173(1) | | | | | >141(0.025) | | 166(0.0063) | >148(0.025) |
| d 1, ip | | 252(7.5) | 155(0.25) | | 175(0.25) | | 182(0.05) | >193(2) | 262(0.0125) | 183(0.05) |
| d 1, iv | | 185(10) | 152(0.5) | | 157(0.5) | | >143(0.062) | 166(2.5) | 152(0.05) | |
| q4d 1, 5,9, ip | | 257(4) | | | | | 224(0.05) | | | |
| q4d 1, 5,9, po | | | | | | | 175(0.05) | | >158(0.1) | |
| qd 1-9, ip ip B16d | | >285(2) | | | | | 209(0.0125) | | >360(0.0063) | 267(0.025) |
| d 1, ip | | >197(20) | | | | | | | >138(0.0063) | 149(0.025) |
| q4d 5, 9,13, ip ip B16 | | 129,146(3) | | | | | | | 123(0.0125) | 121(0.025) |
| d 1, ip | 195(4) | 292(4) | 135(0.25) | 121(0.25) | 138(0.15) | 131(0.0375) | | | | |

*Prior Compounds — For comparison.
(1) 3'-deamino-3'-(4"-morpholinyl)-13-dihydrodaunorubicin
(2) 3'-deamino-3'-(4"-morpholinyl)doxorubicin
(3) 3'-deamino-3'-(4"-morpholinyl)-5-iminodoxorubicin
(4) 3'-deamino-3'-(4"-morpholinyl)-daunorubicin (mistake in US)

The compounds of this invention, including the salts thereof can be administered by any available route, including oral and parenteral (intravenous, intraperitoneal, subcutaneous, and intramuscular) administration. Parenteral administration, especially intravenous administration, has historically been the mode of choice and this is preferred. The dosing regimen and amount administered is sufficient to ameleriorate the leukemia or other type of cancer against which the compounds hereof are effective. For example, in the treatment of lower test animals, a dosage of a compound of the present invention within the range from about 0.0010 mg/kg to about 25 mg/kg per day should be sufficient to amelerioriate leukemia. The upper dosage limit is that imposed by toxic side effects and can be determined by trial and error for the animal to be treated. In general, the dosage with compounds of this invention will be lower than (e.g. 1/20 to 1/200 times) that required with the parent compounds. Dosing regimens of one dose every 2 to 7 days are effective while shorter intervals, say one day or less, between dosings may be used as well.

To facilitate administration, the compounds of this invention, including the salts thereof, can be provided in pharmaceutical composition form, and particularly in unit dosage form. While the compounds can be administered per se, it is more common to administer them in conjunction with a pharmaceutically acceptable carrier which dilutes the compound and facilitates handling. The term "pharmaceutically acceptable" means that the carrier (as well as the resulting composition) is sterile and nontoxic.

For oral dosage, the carrier or diluent can be solid, semisolid, or liquid, and can serve as a vehicle, excipient, or medium for the agent as described in pharmacology texts. For parenteral administration, the compound is dissolved or suspended in a suitable injectable liquid medium as is known in the art.

In the preparation of these dosage forms, one can use the art accepted techniques for formulating water-soluble pharmaceutical agents (in the case of salts) and water-insoluble agents (in the case of the free bases). For example, injectable materials can be formulated as follows.

| Formulation A: | |
|---|---|
| Sterile Suspension in Aqueous Vehicle for Injection | Mg |
| Compound of Examples 1, 2, 3, 4, 5, 6, 9 or 10 as a suspendable powder | 3 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 mL | |

| Formulation A': | |
|---|---|
| Sterile Suspension in Aqueous Vehicle for Injection | Mg |
| "3'-Deamino-3'-(3"-cyano-4"-morpholinyl) doxorubicin of Example 4 | 0.5 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 mL | |

| Formulation B: | |
|---|---|
| Sterile Solution in Aqueous Carrier System for Injection | Mg |
| Compound of Example 7 | 4 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 mL | |

Simimarly, one could formulate tablets for oral administration as follows.

| Formulation C: | |
|---|---|
| Tablet Formulation | Mg |
| Compound of Example 7 | 5.0 |
| Lactose | 91 |
| Cornstarch (dried) | 51.5 |
| Gelatin | 2.5 |
| Magnesium stearate | 1.0 |

The compound of Example 7 is powdered and passed through a mesh sieve and well mixed with the lactose and 30 mg of the cornstarch, both passed through a sieve.

The mixed powders are massed with a warm gelatin solution, prepared by stirring the gelatin in water and heating to form a 10% w/w solution. The mass is granulated by passing through a sieve, and the moist granules dried at 40° C.

The dried granules are re-granulated by passing through a sieve and the balance of the starch and the magnesium stearate is added and thoroughly mixed.

The granules are compressed to produce tablets each weighing 150 mg.

Capsules could be formulated as follows.

| Formulation D: | |
|---|---|
| Capsule Formulation | Mg |
| Compound of Example 8 | 10 |
| Lactose | 190 |

| Formulation D': | |
|---|---|
| Capsule Formulation | Mg |
| 3'-Deamino-3'-(3"-cyano-4"-morpholinyl) doxorubicin of Example 4(C) | 1 |
| Lactose | 199 |

Compound of Example 8 or 4(C) and lactose are passed through a sieve and the powders well mixed together before filling into hard gelatin capsules of suitable size, so that each capsule contains 200 mg of mixed powders.

We claim:

1. A compound of the formula

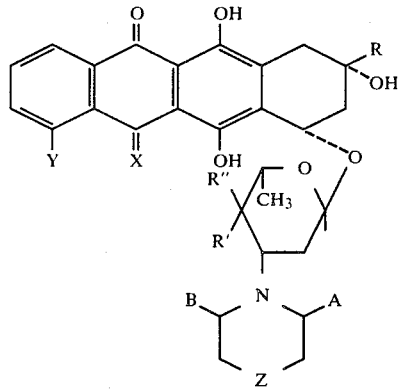

wherein
R is —CO—CH$_3$, —CHOH—CH$_3$, —CO—CH$_2$OH, or —CHOH—CH$_2$OH; hydroxy; a 1 to 3 carbon alkyl; a 1 to 3 carbon terminal hydroxyalkyl; a 2 to 7 carbon organic acid ester or diester of —CO—CH$_2$OH, —CHOH—CH$_2$OH, or —CHOH—CH$_3$; the groups —COCH$_2$OH, —CHOHCH$_2$OH or —CHOHCH$_3$ having a 1 to 6 carbon alkyl or aryl ether replacement of one or more hydroxyls; or 13-ketimine derivative of —CO—CH$_3$ or —CO—CH$_2$OH;
Y is methoxy or hydrogen;
X is =O or =NH;
R' and R" together are a hydrogen and a hydroxy, both are hydrogens, or R' is O-methoxy and R" is hydrogen;
B is CN, or B and the hydrogen bonded to the same carbon taken together are =O; or
B and R' taken together are the oxygen bridge —O—; and
A is cyano;
Z is oxygen, sulfur, CH$_2$, or

wherein R''' is a 1 to 3 carbon alkyl,
and the pharmaceutically acceptable acid addition salts therof.

2. The compound of claim 1 wherein R is COCH$_3$, COCH$_2$OH, —CHOHCH$_3$ or —CHOHCH$_2$OH.

3. The compound of claim 2 which is 3'-deamino-3'-(3"-cyano-5"-oxo-4"-morpholinyl) doxorubicin.

4. The compound of claim 2 which is 3'deamino-3'-(3",5"-dicyano-4"-morpholinyl) doxorubicin.

5. The compound of claim 2 which is 3'deamino-4',5"-anhydro-3'-(3"-cyano-5"-hydroxy-4"-morpholinyl) doxorubicin.

6. The compound of claim 2 which is 3'deamino-3'-(3"-cyano-5"-oxo-4"-morpholinyl) daunorubicin.

7. The compound of claim 2 which is 3'deamino-3'-(3",5"-dicyano-4"morpholinyl) daunorubicin.

8. The compound of claim 2 which is 3'deamino-4',5"-anhydro-3'-(3"-cyano-5"-hydroxy-4"-morpholinyl) daunorubicin.

* * * * *